(12) United States Patent
Bradley et al.

(10) Patent No.: US 8,880,170 B2
(45) Date of Patent: Nov. 4, 2014

(54) AUTONOMIC MODULATION USING PERIPHERAL NERVE FIELD STIMULATION

(71) Applicant: Cardiac Pacemakers, Inc., St. Paul, MN (US)

(72) Inventors: Kerry Bradley, Glendale, CA (US); Rafael Carbunaru, Valley Village, CA (US); Jason J. Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/686,336

(22) Filed: Nov. 27, 2012

(65) Prior Publication Data

US 2013/0138167 A1    May 30, 2013

Related U.S. Application Data

(60) Provisional application No. 61/564,469, filed on Nov. 29, 2011.

(51) Int. Cl.
| | |
|---|---|
| *A61N 1/362* | (2006.01) |
| *A61N 1/36* | (2006.01) |
| *A61N 1/39* | (2006.01) |
| *A61N 1/372* | (2006.01) |

(52) U.S. Cl.
CPC ......... *A61N 1/36114* (2013.01); *A61N 1/37235* (2013.01); *A61N 1/3621* (2013.01); *A61N 1/37282* (2013.01); *A61N 1/3627* (2013.01); *A61N 1/36053* (2013.01); *A61N 1/36117* (2013.01); *A61N 1/3962* (2013.01); *A61N 1/36146* (2013.01); *A61N 1/3605* (2013.01); *A61N 1/36057* (2013.01); *A61N 1/36139* (2013.01); *A61N 1/37288* (2013.01)
USPC ............................................... 607/9; 607/44

(58) Field of Classification Search
CPC . A61N 1/0504; A61N 1/0551; A61N 1/3605; A61N 1/36114; A61N 1/36117; A61N 1/3621; A61N 1/3627
USPC ................................ 607/2, 4, 9, 44, 116, 117
See application file for complete search history.

(56) References Cited

U.S. PATENT DOCUMENTS

| | | | | |
|---|---|---|---|---|
| 5,792,187 A | * | 8/1998 | Adams | ............................... 607/5 |
| 6,058,331 A | * | 5/2000 | King | ............................... 607/62 |

(Continued)

FOREIGN PATENT DOCUMENTS

| | | |
|---|---|---|
| WO | WO-2010051385 A1 | 5/2010 |
| WO | WO-2010088539 A1 | 8/2010 |
| WO | WO-2013082022 A1 | 6/2013 |

OTHER PUBLICATIONS

"International Application Serial No. PCT/US2012/066638, International Search Report mailed Apr. 5, 2013", 3 pgs.

(Continued)

*Primary Examiner* — Carl H Layno
*Assistant Examiner* — Eugene Wu
(74) *Attorney, Agent, or Firm* — Schwegman Lundberg & Woessner, P.A.

(57) ABSTRACT

Some embodiments provide a system, comprising a peripheral nerve field modulation (PNFM) therapy delivery system, PNFM electrodes configured to be implanted subcutaneously, and a controller. The PNFM electrodes are electrically connected to the PNFM therapy system. The PNFM therapy delivery system and the PNFM electrodes are configured to deliver current and/or control the field potentials at one or more peripheral nerve fields. The controller is configured to control the PNFM therapy delivery system to deliver a PNFM therapy to the one or more peripheral nerve fields. The controller includes a scheduler configured to control timing of the PNFM therapy.

25 Claims, 15 Drawing Sheets

(56) References Cited

U.S. PATENT DOCUMENTS

| | | |
|---|---|---|
| 7,260,431 B2 | 8/2007 | Libbus et al. |
| 7,493,161 B2 | 2/2009 | Libbus et al. |
| 7,509,166 B2 | 3/2009 | Libbus |
| 7,542,800 B2 | 6/2009 | Libbus et al. |
| 7,551,958 B2 | 6/2009 | Libbus et al. |
| 7,587,238 B2 | 9/2009 | Moffitt et al. |
| 7,657,312 B2 | 2/2010 | Pastore et al. |
| 7,672,728 B2 | 3/2010 | Libbus et al. |
| 7,689,286 B2 | 3/2010 | Pastore et al. |
| 2003/0078633 A1* | 4/2003 | Firlik et al. ............ 607/46 |
| 2004/0162590 A1* | 8/2004 | Whitehurst et al. ...... 607/17 |
| 2006/0041283 A1* | 2/2006 | Gelfand et al. ......... 607/44 |
| 2007/0073357 A1* | 3/2007 | Rooney et al. ......... 607/46 |
| 2007/0260283 A1 | 11/2007 | Li |
| 2008/0086174 A1 | 4/2008 | Libbus et al. |
| 2009/0281595 A1* | 11/2009 | King et al. ............. 607/46 |
| 2009/0281596 A1* | 11/2009 | King et al. ............. 607/46 |
| 2009/0318986 A1* | 12/2009 | Alo et al. .............. 607/4 |
| 2010/0036447 A1 | 2/2010 | Zhang et al. |
| 2010/0114195 A1* | 5/2010 | Burnes et al. ........... 607/4 |
| 2010/0125314 A1* | 5/2010 | Bradley et al. ......... 607/59 |
| 2010/0198284 A1* | 8/2010 | Zhou et al. ............ 607/4 |
| 2011/0022114 A1 | 1/2011 | Navarro et al. |
| 2011/0218586 A1 | 9/2011 | Li |
| 2012/0041511 A1* | 2/2012 | Lee ................... 607/46 |

OTHER PUBLICATIONS

"International Application Serial No. PCT/US2012/066638, Written Opinion mailed Apr. 5, 2013", 7 pgs.

* cited by examiner

AUTONOMIC MODULATION USING PERIPHERAL NERVE FIELD STIMULATION

CROSS-REFERENCE TO RELATED APPLICATION

This application claims the benefit of U.S. Provisional Application No. 61/564,469, filed on Nov. 29, 2011, under 35 U.S.C. §119(e), which is hereby incorporated by reference in its entirety.

TECHNICAL FIELD

This application relates generally to medical devices and, more particularly, to systems, devices and methods for using peripheral nerve field stimulation to provide autonomic modulation.

BACKGROUND

Therapies that are based on autonomic modulation have shown efficacy in a variety of cardiovascular diseases in both preclinical and clinical studies. The autonomic balance can be modulated to have more parasympathetic tone by stimulating parasympathetic targets or inhibiting sympathetic targets, and can be modulated to have more sympathetic tone by stimulating sympathetic targets or inhibiting parasympathetic targets.

Sympathetic overactivation is involved in a variety of cardiovascular disease, such as ventricular arrhythmias, myocardial infarction (MI), heart failure (HF), etc. For example, vagus nerve stimulation, which generally increases parasympathetic tone, has been proposed as a therapy for cardiovascular problems such as cardiac rhythm management, myocardial infarction and ischemia, heart failure (HF), blood pressure control such as to treat hypertension, and sleep disordered breathing, and also has been proposed as a therapy for epilepsy, depression, pain, migraines, eating disorders/obesity, and movement disorders.

Spinal cord stimulation (SCS) has been proposed to control pain control, such as ischemic pain conditions. SCS has been shown to have a sympatholytic effect. These effects are mediated either directly through modulation of sympathoefferent spinal circuits or indirectly by peripheral vasodilation via spinal-mediated nerve traffic, similar to dorsal root reflexes.

SUMMARY

Some embodiments provide a system, comprising a peripheral nerve field modulation (PNFM) therapy delivery system, PNFM electrodes configured to be implanted subcutaneously, and a controller. Subcutaneous, as used herein, refers to a non-intrathoracic space (e.g. within the tissue layers outside of or adjacent to the rib cage). The PNFM electrodes are electrically connected to the PNFM therapy system. The PNFM therapy delivery system and the PNFM electrodes are configured to deliver current and/or control the field potentials at one or more peripheral nerve fields. That is, the PNFM therapy delivery system and the PNFM electrodes are configured to deliver current at one or more peripheral nerve fields, or are configured to control the field potentials at one or more peripheral fields, or are configured to both deliver current at one or more peripheral nerve fields and control the field potentials at one or more peripheral fields. The controller is configured to control the PNFM therapy delivery system to deliver a PNFM therapy to the one or more peripheral nerve fields. The controller includes a scheduler configured to control timing of the PNFM therapy.

Some embodiments provide a method, comprising delivering neural modulation for a cardiovascular therapy. Delivering neural stimulation for the cardiac therapy includes delivering a peripheral nerve field modulation (PNFM) to peripheral nerve fields of one or more of the intercostal nerves extending to and from a T1-T5 region of a spinal cord.

Some embodiments provide method for delivering a heart failure therapy, comprising modulating peripheral nerve fields of intercostal nerves extending to and from a T1-T5 region of a spinal cord.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1A:
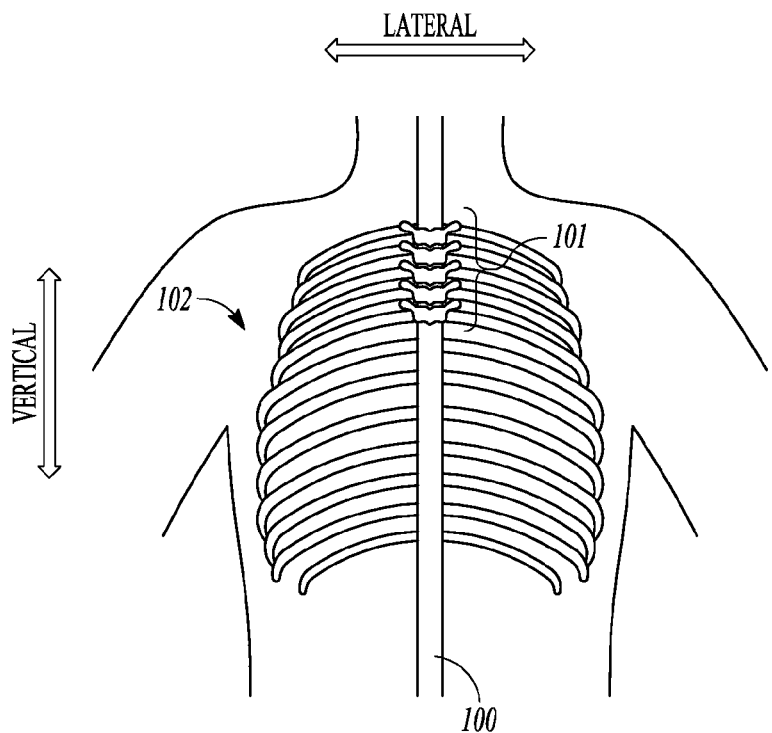
FIGS. 1A and 1B illustrate a spinal column.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The autonomic nervous system (ANS) regulates "involuntary" organs (in contrast to the somatic nervous system, responsible for volitional body system control e.g., the contraction of skeletal muscles). Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS is divided into the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and can work in concert with the somatic nervous system.

The ANS has direct influences on cardiac performance. The heart rate and contractility are increased when the sympathetic nervous system is stimulated, and are decreased when the sympathetic nervous system is inhibited (or the parasympathetic nervous system is stimulated).

Stimulating the sympathetic and parasympathetic nervous systems can have effects other than heart rate and blood pressure. For example, stimulating the sympathetic nervous system, depending upon the site of stimulation, can dilate the pupil, reduce saliva and mucus production, relax the bronchial muscle, reduce the successive waves of involuntary contraction (peristalsis) of the stomach and the motility of the stomach, increase the conversion of glycogen to glucose by the liver, decrease urine secretion by the kidneys, and relax the wall and closes the sphincter of the bladder. Stimulating the parasympathetic nervous system has different and typically opposite effects to stimulation of the sympathetic nervous system: constriction of the pupil, increased saliva and mucus production, contraction of the bronchial muscle, increased secretions and motility in the stomach and large intestine, increased digestion in the small intestine, increased urine secretion, and contraction the wall and relaxation of the sphincter of the bladder. The functions associated with the sympathetic and parasympathetic nervous systems are many and can be complexly integrated with each other.

Neural stimulation may be used to treat a variety of cardiovascular disorders, including heart failure, post-MI remodeling, and hypertension. These conditions are briefly described below.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension may be defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Figure 1B:
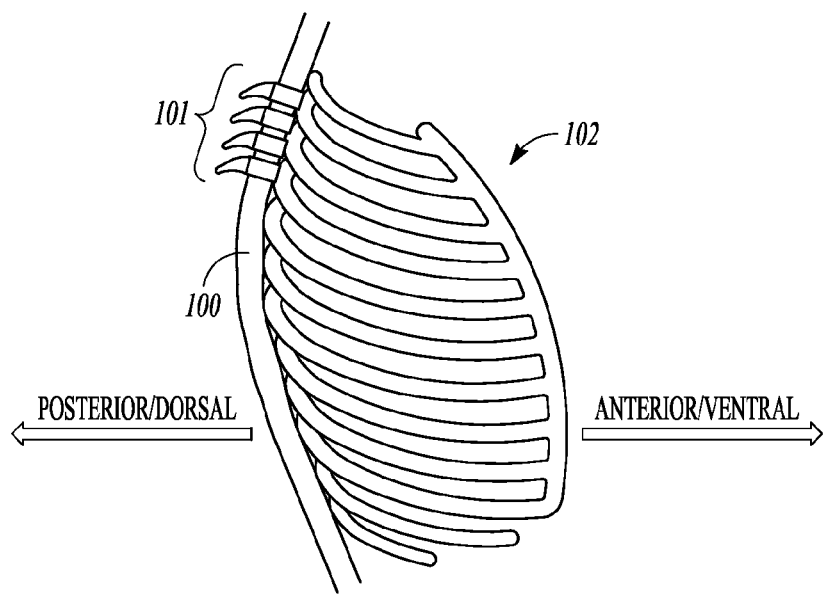

FIG. 1A illustrates a spinal column 100, including the T1-T5 vertebrae 101, and further illustrates ribs 102 from a posterior or dorsal perspective. FIG. 1B illustrates a side view of the spinal column, including the T1-T5 vertebrae 101 of the column, and the ribs 102. These figures also illustrate a lateral axis, a vertical axis in the cranial (up) or caudal (down) direction, and a posterior or dorsal direction and an anterior or ventral direction. The spinal column includes cervical, thoracic and lumbar areas. Vertebrae form the building blocks of the spinal column and protect the spinal cord. T1-T5 are the uppermost (cranial) portion of the thoracic area of the spinal column. Projections from T1-T5 innervate the heart, and are sympathetic. Various embodiments of the present subject matter stimulate nerves extending to and from T1-T5, to ultimately reduce neural activity in the cardiac efferent nerves and thus reduce the effective sympathetic tone in the regions of the body innervated by these nerves. Various embodiments target the T1-T5 region to inhibit sympathetic effects for cardiovascular disease applications. Increased efferent sympathetic activity increases heart rate and contractility. Afferent activity (e.g. pain signals) for the heart tissue also go through spinal segments T1-T5. Other regions may be targeted for other applications (e.g. treatment for hypertension, diabetes, obesity, etc.).

Figure 2:
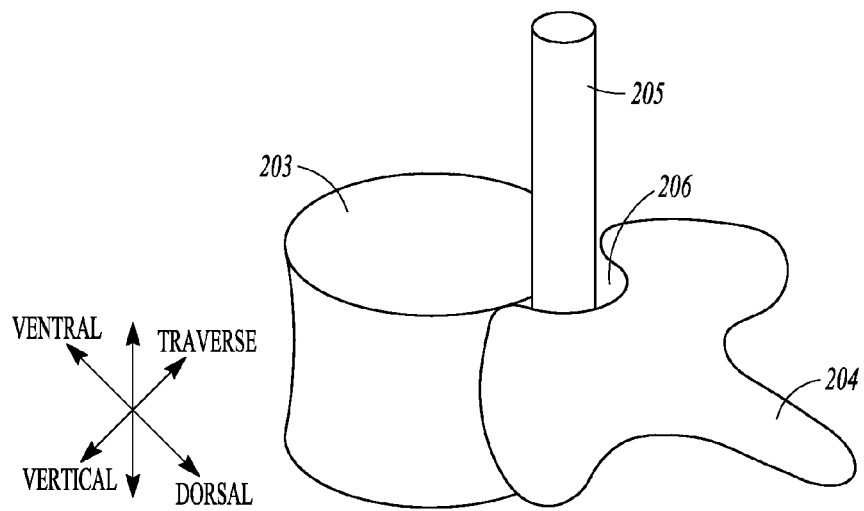
FIG. 2 illustrates a perspective view of a portion of the spinal column.

FIG. 2 illustrates a perspective view of a portion of the spinal column. As illustrated, the vertebrae includes a vertebral body 203 and a bony projection containing a foramen 204 attached to the vertebral body 203. The stacked vertebrae provide a vertebral canal that protects the spinal cord 205. The spinal cord is nerve tissue that carries neural messages between the brain and parts of the body. Nerve roots branch off and exit the spine on both sides through spaces between the vertebra. The spinal cord is surrounded by dura mater, which holds spinal fluid that surrounds the spinal cord. The space between the dura mater and the inner wall of the vertebral canal is referred to as epidural space 206. A spinal cord stimulator (SCS) stimulates the spinal cord, and some SCS embodiments use electrodes in the epidural space to stimulate neural targets in the spinal cord. Spinal cord stimulation may also be referred to as spinal cord modulation (SCM).

Figure 3:
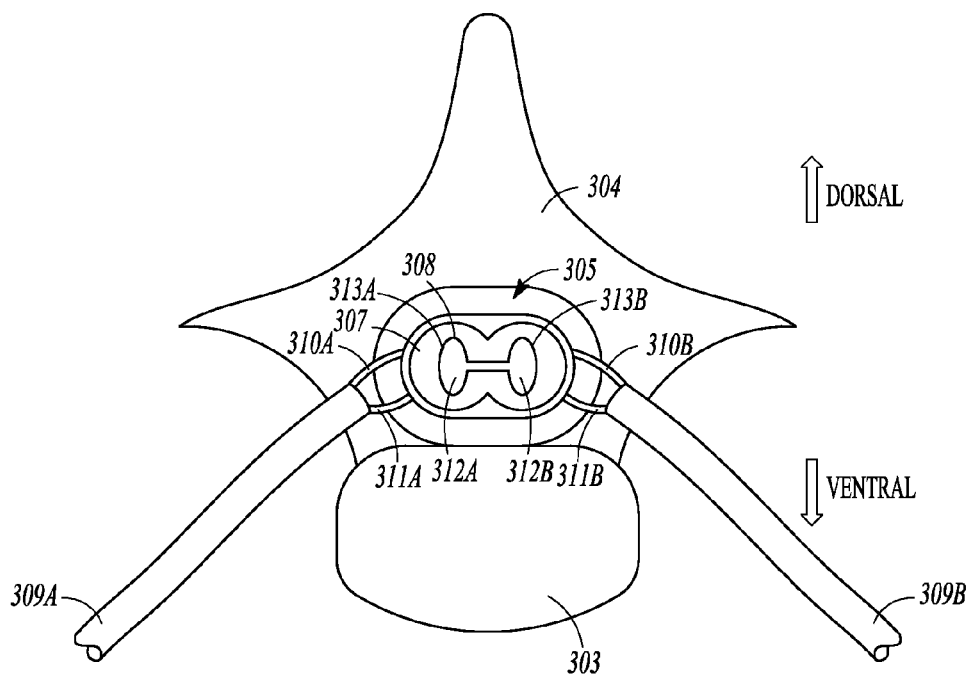
FIG. 3 illustrates a top view of a cross section of a vertebra in the spinal column.

FIG. 3 illustrates a top view of a cross section of a vertebra in the spinal column. The vertebra includes a vertebral body 303 and a bony ring 304 that includes the spinous process. The vertebrae provide a spinal canal that contains the spinal cord. The illustrated spinal cord includes white matter 307 and gray matter 308. Spinal nerves 309A, 309B extend from the sides of the spinal column. Each spinal nerve 309A, 309B has a dorsal nerve root 310A, 310B and a ventral nerve root 311A, 311B. The front or ventral gray column of the spinal cord is referred to as the ventral horn 312A, 312B, which is a longitudinal subdivision of gray matter in the anterior part of each lateral half of the spinal cord that contains neurons giving rise to motor fibers of the ventral roots of the spinal nerves. The posterior gray column of the spinal cord is referred to as the dorsal horn 313A, 313B, which is a longitudinal subdivision of gray matter in the dorsal part of each lateral half to the spinal cord that receives terminals from some afferent fibers of the dorsal roots of the spinal nerves. The ventral root 311A, 311B is the efferent motor root of a spinal nerve. The dorsal root 310A, 310B is the afferent sensory root of the spinal nerve. The ventral root joins with the dorsal root to form a mixed spinal nerve 309A, 309B. Along the spinal exit of the dorsal root is the dorsal root ganglion which contains the neuron cell bodies of the nerve fibers conveyed by the root. Spinal nerves carry motor, sensory, and autonomic signals between the spinal cord and the body. Each spinal nerve is formed by the combination of nerve fibers from the dorsal and ventral roots of the spinal cord. The dorsal roots carry afferent sensory axons, while the ventral roots carry efferent motor axons. Outside the vertebral column, the nerve divides into branches. The dorsal ramus contains nerves that serve the dorsal portions of the trunk carrying visceral motor, somatic motor, and sensory information to and from the skin and muscles of the back. The ventral ramus contains nerves that serve the remaining ventral parts of the trunk and the upper and lower limbs carrying visceral motor, somatic motor, and sensory information to and from the ventrolateral body surface, structures in the body wall, and the limbs.

The afferent sympathetic pathway includes neuron bodies in the dorsal root ganglia, and neuron bodies in the dorsal horn. The efferent sympathetic pathway includes preganglionic motor neuron bodies in the intermediolateral column of the spinal cord from T1 to T4/T5, and postganglionic motor neuron bodies in superior, middle and inferior cervical ganglias and in cell T1 thoracic ganglias from T1 to T4/T5.

Figure 4:
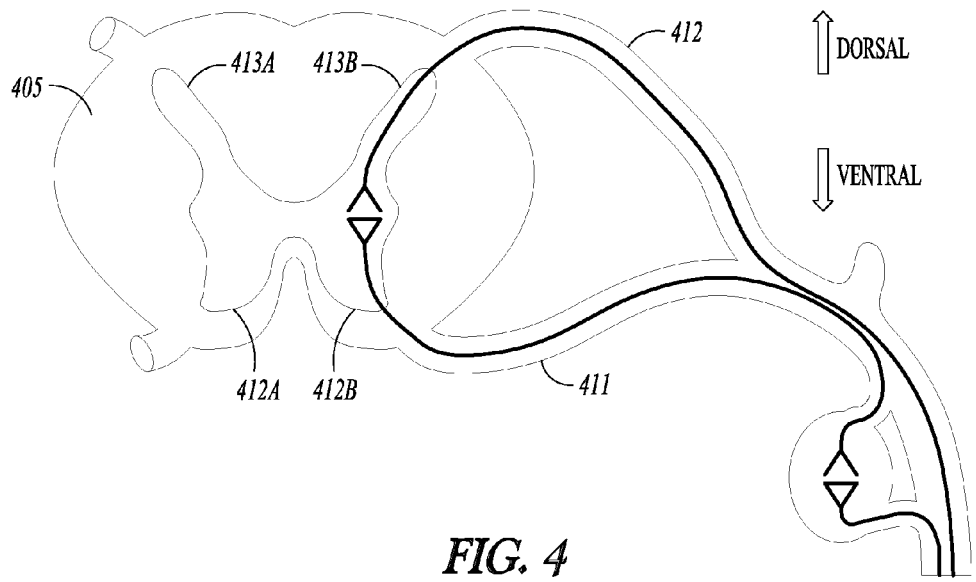
FIG. 4 illustrates sympathetic pathways extending from ventral and dorsal nerve roots.

FIG. 4 illustrates sympathetic pathways extending from ventral and dorsal nerve roots. The gray matter of the spinal cord 405 includes ventral horns 412A, 412B and dorsal horns 413A, 413B. The ventral root 411 is the efferent motor root of a spinal nerve. The dorsal root 412 is the afferent sensory root of the spinal nerve. The ventral root joins with the dorsal root to form a mixed spinal nerve.

Figure 5:
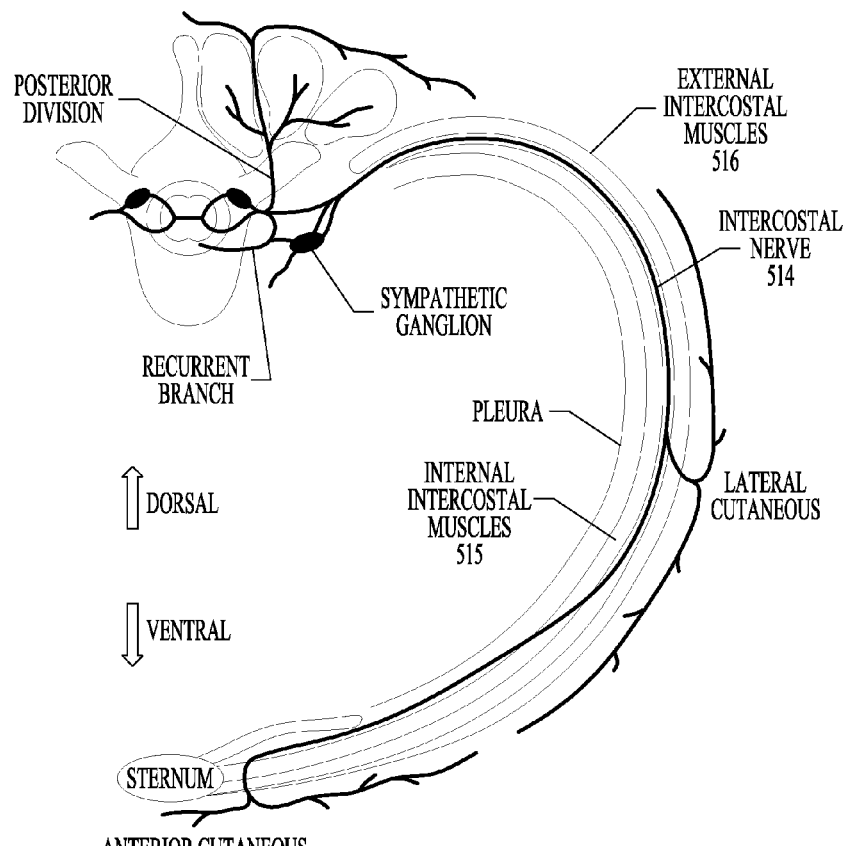
FIG. 5 illustrates intercostal nerves from a top perspective.

FIG. 5 illustrates intercostal nerves from a top perspective. Intercostal nerves are the ventral or anterior divisions of the thoracic spinal nerves, both sensory and motor, from T1 to T11. As illustrated, the intercostal nerves 514 run between the internal intercostal muscles 515 and the external intercostal muscles 516.

Figure 6:
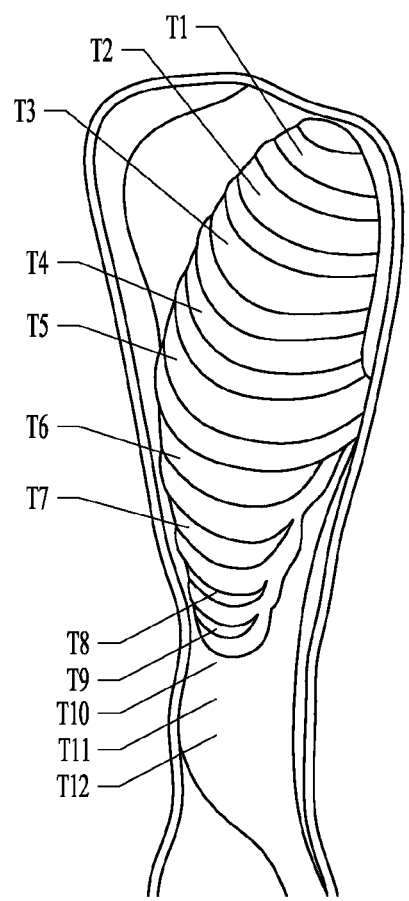
FIG. 6 generally illustrates anterior divisions of the thoracic spinal nerves, labeled T1-T12, from a front view of the body.

FIG. 6 generally illustrates anterior divisions of the thoracic spinal nerves, labeled T1-T12, from a front view of the body. The T1-T11 ventral divisions of the thoracic spinal nerves are intercostal nerves. Some embodiments target any one or any combination of the T1-T5 intercostal nerves. T1-T2 nerves supply fibers to the upper limbs in addition to their thoracic branches, and T3-T6 nerves supply fibers to the wall of the thorax. T7-T12 nerves innervate other lower portions of the body. The anterior division of the first thoracic nerve divides into two branches, where one branch leaves the thorax in front of the neck of the first rib and enters the brachial plexus, and the other smaller branch runs along the first intercostal space and ends on the front of the chest as the first anterior cutaneous branch of the thorax. The anterior divisions of the second, third, fourth, fifth, and sixth thoracic nerves and the small branch from the first thoracic are thoracic intercostal nerves. The muscles that one particular spinal root supplies are that nerve's myotome. A dermatome is an area of skin that is mainly supplied with the nerve fibers from a single, posterior, spinal root. The spinal nerve relays sensation (including pain) from a particular region of skin to the brain.

Figure 7:
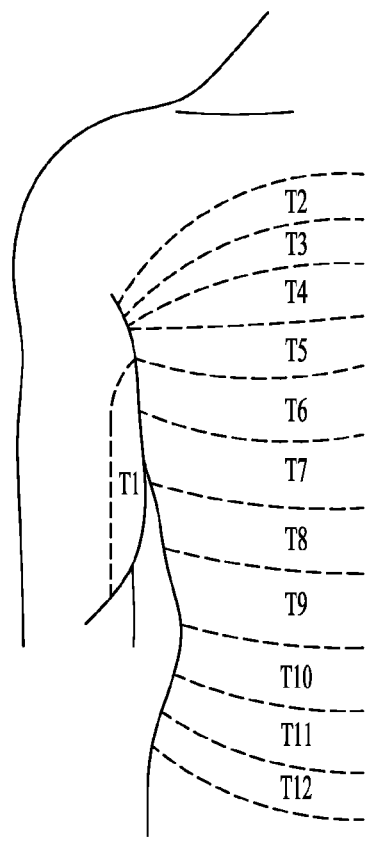
FIG. 7 generally illustrates the dermatomes of the intercostal nerves.

FIG. 7 generally illustrates the dermatomes of the intercostal nerves. The labels T1-T12 identify the dermatome with its intercostal nerve. The dermatomes are like a series of ribbons covering the thorax, where each ribbon is supplied by a different spinal nerve. A similar area innervated by a peripheral nerve is called a peripheral nerve field, which refers to an area of skin innervated by a simple peripheral nerve. Peripheral nerves are nerves outside of the brain and spinal cord. Intercostal nerves are peripheral nerves, as they extend to and from the spinal cord into the intercostal region. A peripheral nerve field can also be described as cutaneous nerve distribution. Peripheral nerve field stimulation (PNFS) refers to stimulation configured to stimulate peripheral nerve field(s). PNFS is delivered using electrodes positioned in a subdermal level to stimulate a targeted region of subcutaneous nerve fibers. The precise neural target, however, is not identified for stimulation. PNFS has been proposed for pain management, including management of angina.

PNFS may also be referred to as peripheral nerve field modulation (PNFM). A PNFM system may be configured to deliver current at one or more peripheral fields, or to control field potentials at one or more peripheral fields, or to both deliver current at one or more peripheral field and control field potentials at one or more peripheral fields. Various embodiments of the present subject matter use PNFS alone or in conjunction with SCS to increase an anti-sympathetic effect of a neural stimulation therapy. Such antisympathetic effects may be put to use to treat autonomic disorders. For example, some embodiments use PNFS alone or in conjunction with SCS to increase on antisympathetic effect on intracardiac neurons. SCS and peripheral nerve stimulation have been shown to reduce the sympathetic effects on the heart. For example, some embodiments use PNFS alone or in conjunction with SCS to increase an antisympathetic effect in patients with an elevated sympathetic tone such as patients with congestive heart failure (CHF). Electrical stimulation may be used alone or as an adjunct to drugs and other procedures to treat elevated sympathetic tone in patients with CHF.

Figure 8:
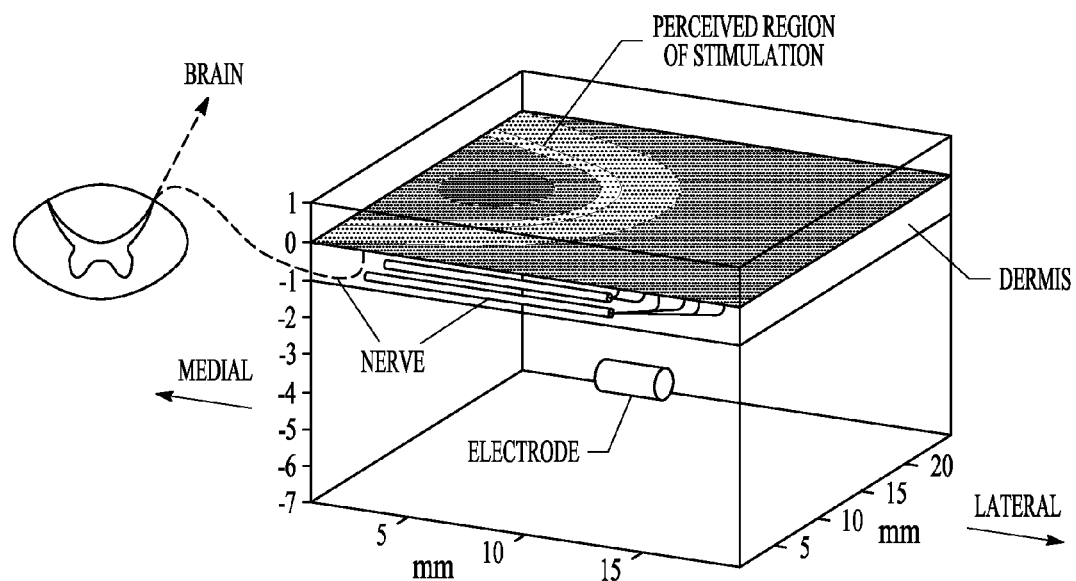
FIG. 8 generally illustrates positioning of a subcutaneous electrode with respect to nerves innervating the dermis and adjacent tissues.
Figure 9:
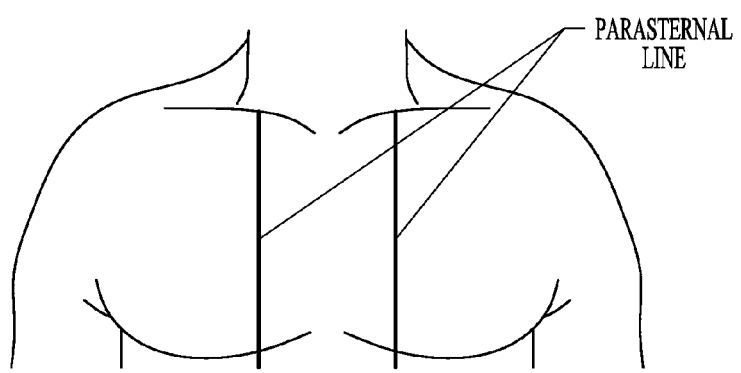
FIG. 9 illustrates a parasternal line.

The PNFS electrodes may be placed in the subcutaneous space along the sternum to span the multiple upper thoracic dermatomes (T1-T5), generally illustrated in FIG. 7, along the posterior axial spine just off midline to the left side of the spine axis. Multiple PNFS electrodes may be placed. For example, a PNFS electrode may be placed at the sternum site and another PNFS electrode may be placed off-midline near the axial spine. Field stimulation electrodes may be placed parasternal, precordial, posterior paraspinal or intercostal. FIG. 8 generally illustrates positioning of a subcutaneous electrode with respect to nerves innervating the dermis and adjacent tissues. SCS electrodes, if used, are placed in the cervical and/or upper thoracic spine. PNFS electrodes are placed over or near intercostal nerves. FIG. 9 illustrates a parasternal line. Precordial is the portion of the body over the heart and lower chest, paraspinal is adjacent to the spinal column, and intercostal is situated or extending between the ribs.

Figure 10:
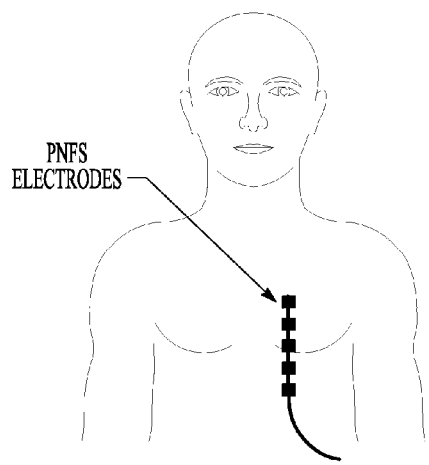
FIG. 10 generally illustrates PNFS electrodes positioned parasternally.
Figure 11:
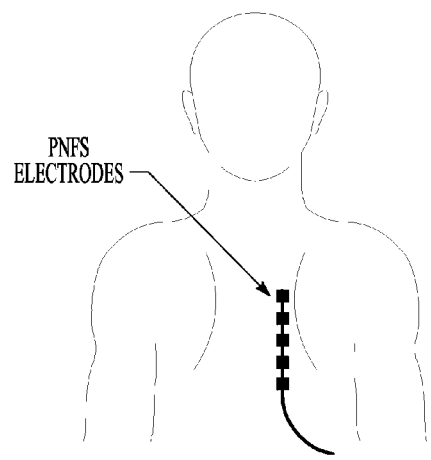
FIG. 11 generally illustrates PNFS electrodes positioned paraspinally or paravertebrally.
Figure 12:
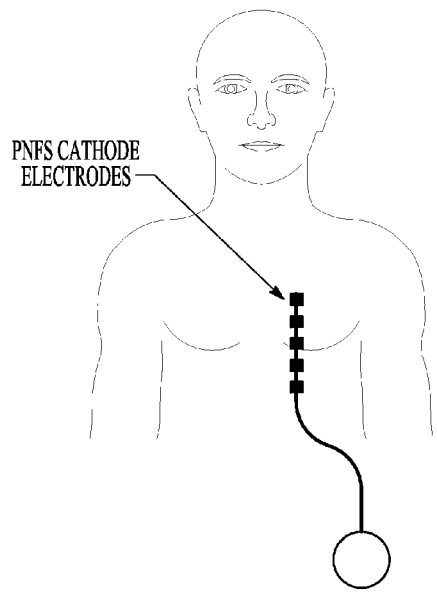
FIG. 12 illustrates an embodiment where the PNFS electrodes are positioned parasternally, similar to FIG. 10.
Figure 13:
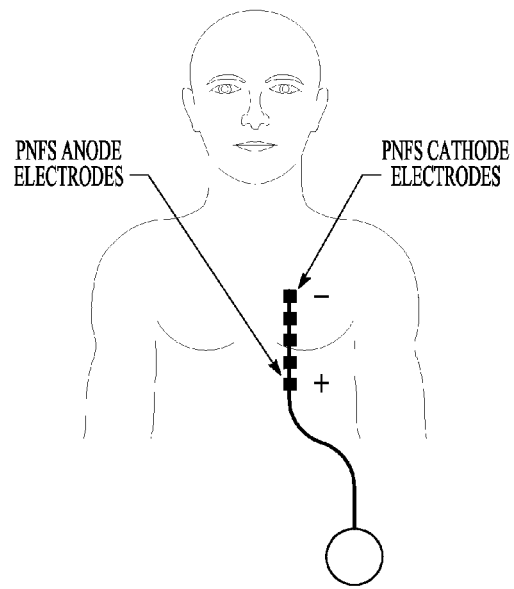
FIG. 13 illustrates an embodiment where the PNFS electrodes are positioned parasternally, similar to FIG. 10.
Figure 14A:
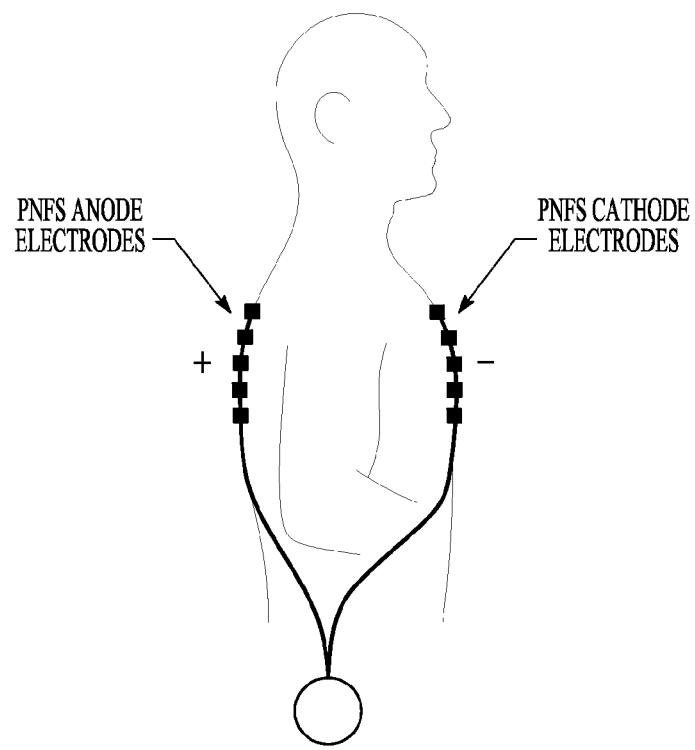
FIGS. 14A and 14B illustrate embodiments that use a cross-lead arrangement, with one lead positioning PNFS electrodes parasternally and another lead positioning PNFS electrodes paraspinally or paravertebrally.
Figure 14B:
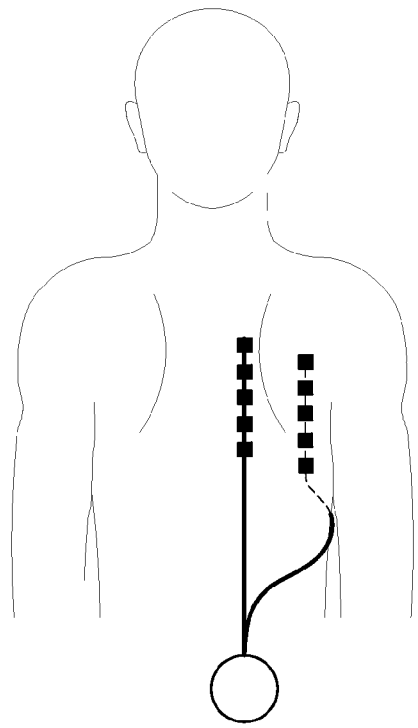

FIG. 10 generally illustrates PNFS electrodes positioned parasternally, and FIG. 11 generally illustrates PNFS electrodes positioned paraspinally or paravertebrally. FIG. 12 illustrates an embodiment where the PNFS electrodes are positioned parasternally, similar to FIG. 10. The system is configured in a monopolar arrangement in which the parasternally-positioned PNFS electrode(s) are electrically connected as a pole, and the pulse generator is the other pole. In the illustrated embodiment, the system is programmed to use the parasternally-positioned PNFS electrodes as a cathode, and to use the pulse generator as an anode. FIG. 13 illustrates an embodiment where the PNFS electrodes are positioned parasternally, similar to FIG. 10. The system is configured in a bipolar arrangement in which the system is programmed to use one or more PNFS electrodes on the lead as a cathode and one or more PNFS electrodes on the lead as an anode. In the illustrated embodiment, the system is configured to use the cranial PNFS electrode(s) on the lead as a cathode and to use the caudal PNFS electrode(s) on the lead as an anode. As generally illustrated in FIGS. 14A and 14B, some embodiments use a cross-lead arrangement, with one lead positioning PNFS electrodes parasternally and another lead positioning PNFS electrodes paraspinally or paravertebrally. In the illustrated embodiment, the system is programmed to use the parasternally-positioned PNFS electrodes as a cathode and to use the paraspinally-positioned PNFS electrodes as an anode. The system may be programmed to provide a variety of stimulation vectors between or among the PNFS electrodes and, in some monopolar configurations, between or among the pulse generator and the PNFS electrode(s).

Field stimulation across the targeted nerves provides an effective mild sympathectomy. It is expected that such field stimulation causes redistribution of coronary blood flow by increasing cardiac arteriolar vessel diameter, decreases total peripheral resistance (again via small blood vessels), reduces systemic catecholamine levels (epinephrine), and stabilizes the intracardiac nervous system.

The field stimulation may be delivered using a frequency within a range of 0.1-100,000 Hz. The stimulation may be continuous or may be delivered in bursts. An example of a burst stimulation protocol is an alternating pattern of 1 second ON and 7 seconds OFF. Some embodiments use burst stimulation protocols with other patterns. The stimulation intensity may vary. For example, the intensity may be at chronic low/subperceptible levels for prophylaxis/preemptive therapy. The stimulation may be at an intermittent high current amplitude and low rate of alternating stimulation ON/stimulation OFF for selective A-delta activation. A-delta nerve fibers are associated with sharp, localized pain. Acupuncture inhibits pain transmission by stimulating A-delta fibers. In an embodiment, by way of example and not limitation, a physician programs a stimulator to run continuously at low amplitude, relatively high rate of alternating stimulation ON/stimulation OFF, and prescribes the patient to periodically (e.g. once per day) activate a brief high amplitude, low frequency program.

In comparison to spinal cord stimulation, field stimulation is less invasive and reduces the likelihood of migration and the risk of reoperation to correct the system for the migration. Field stimulation provides an opportunity to mildly activate A-delta fibers, which may trigger descending inhibition via serotonin release.

Therapies

Various embodiments relate to systems, devices and methods for providing neural stimulation using PNFS alone or using PNFS with SCS. Some embodiments include VNS therapy coordinated with the PNFS therapy, and some embodiments include CRM therapy coordinated with the PNFS therapy. The present subject matter can be implemented in cardiac applications for neural stimulation or in non-cardiac applications for neural stimulation where it is desired to inhibit sympathetic effects. For example, the present subject matter may deliver anti-remodeling therapy through neural stimulation as part of a post-MI or heart failure therapy. Various embodiments provide systems or devices that integrate neural stimulation with one or more other therapies, such as bradycardia pacing, anti-tachycardia therapy, remodeling therapy, and the like.

Some neural stimulation embodiments prevent and/or treat ventricular remodeling by using PNFS, with or without CNS, to stimulate neural targets to inhibit sympathetic activity. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment may cause side effects and may be difficult to control to modulate the effects of the treatment. Embodiments of the present subject matter employ electrostimulatory means to modulate autonomic effects, referred to as anti-remodeling therapy or ART. When delivered in conjunction with ventricular resynchronization pacing, also referred to as remodeling control therapy (RCT), such modulation of autonomic activity may act synergistically to reverse or prevent cardiac remodeling.

Some embodiments treat hypertension using PNFS, with or without CNS stimulation, to stimulate neural target(s) for sustained periods of time sufficient to inhibit sympathetic effects and reduce hypertension. Some embodiments integrate PNFS with various myocardial stimulation therapies. The integration of therapies may have a synergistic effect. Therapies can be coordinated with each other, and sensed data can be shared between the therapies. A myocardial stimulation therapy provides a cardiac therapy using electrical stimulation of the myocardium. Some examples of myocardial stimulation therapies are provided below. The stimulation system may be linked to another neural stimulation device or to a CRM device such as an implantable cardioverter defibrillator (ICD), bradycardia device, or resynchronization device. Linking may be by direct connection, by telemetry, or other interdevice communication techniques (e.g. sensing the other device in the volume conductor of the body and altering device output).

A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients. It is currently believed that this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Figure 15:
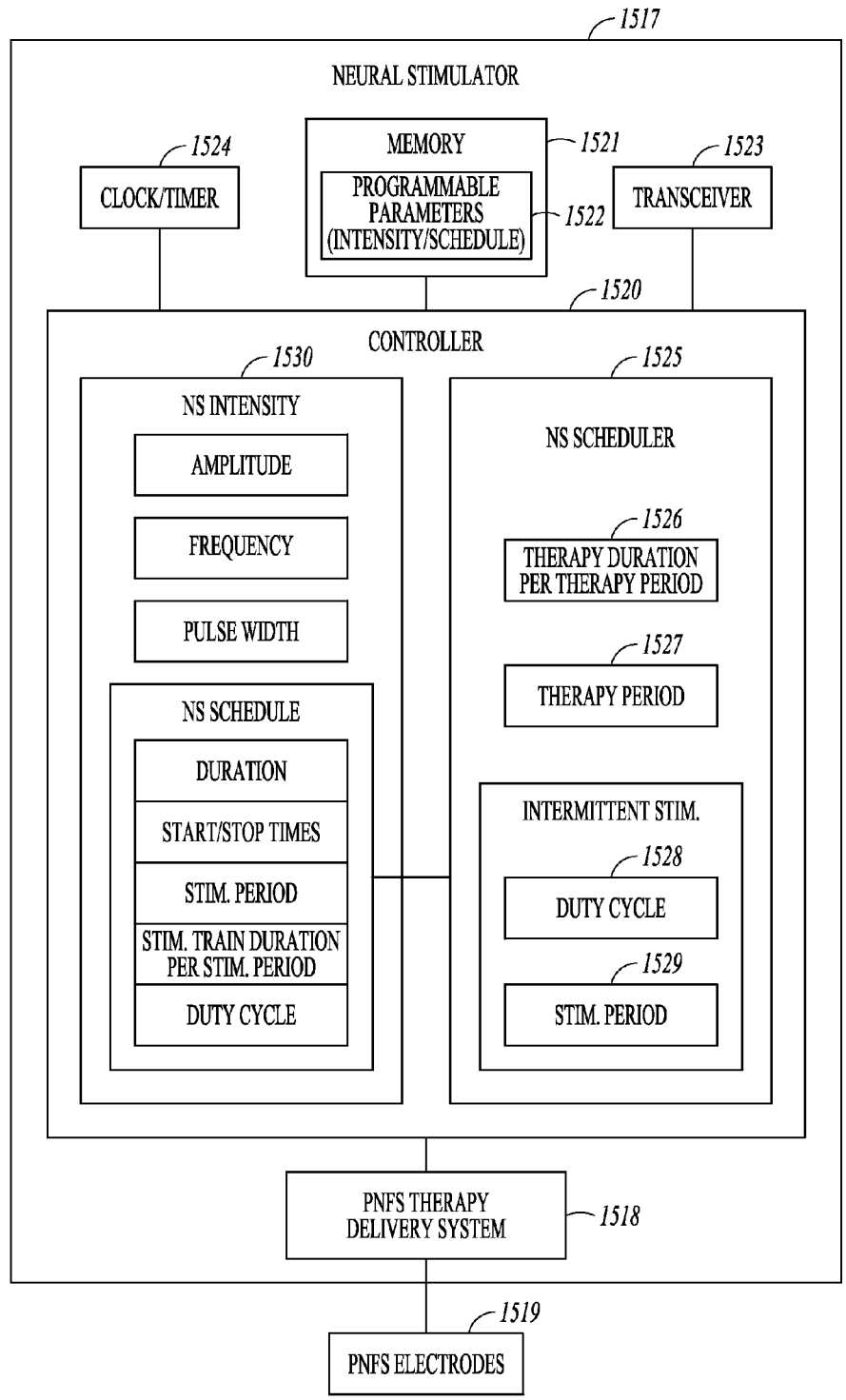
FIG. 15 illustrates an embodiment of a PNFS stimulation device.

In some embodiments PNFS is the only neural stimulation delivered. FIG. 15 illustrates a PNFS stimulation device 1517, according to various embodiments. The illustrated device includes a PNFS therapy delivery system 1518 adapted to deliver a neural stimulation signal to the PNFS electrode(s) 1519 to deliver the PNFS therapy to the desired intercostal nerves. The PNFS therapy delivery system may include pulse generators for delivering electrical pulses through the PNFS electrodes to stimulate peripheral nerve fields. A controller 1520 appropriately controls the neural stimulation therapy delivery system to provide the appropriate neural stimulation signal to the PNFS electrode(s) that results in a desired neural stimulation therapy. The illustrated device includes a memory 1521 to store programmable parameters 1522. The controller implements PNFS therapy using the programmable parameters. Examples of programmable parameters, any one or more of which can be stored in the memory, include a therapy duration parameter, a therapy period, as well as a duty cycle, and a stimulation therapy for intermittent stimulation. The programmable parameters can also include parameters used to adjust the intensity of the neural stimulation therapy, such as amplitude, frequency, pulse width, and stimulation schedule parameters. The illustrated device includes a transceiver 1523 adapted to communicate with an external device (e.g. programmer) for use in receiving programming instructions. In some embodiments, the device may include at least one port for receiving neural stimulation therapy inputs or neural stimulation feedback inputs (including both therapy and feedback inputs according to some embodiments). The input can receive a communication from a device programmer, for use by a physician or patient in changing the programmable parameters based on observed conditions. The input can receive a feedback from physiologic sensors used to monitor physiologic responses to the neural stimulation. Examples of such sensors used to provide feedback include, but are not limited to, heart rate, blood pressure and respiration sensors.

The illustrated device includes a clock/timer 1524, used by the controller to control timing of the neural stimulation signals for the neural stimulation therapy. The illustrated controller includes a neural stimulation scheduler 1525, which uses the clock/timer and schedule parameter(s) to control the stimulation delivered by the delivery system. In some embodiments, the neural stimulation controller controls the neural stimulation delivered using PNFS electrodes to provide a chronic therapy for a chronic condition, such as heart failure. The scheduler uses at least one schedule parameter. Some scheduler embodiments use a duration parameter(s) 1526 to control the therapy duration per therapy period, and some scheduler embodiments use a therapy period parameter 1527 to control a duration of time before a subsequent therapy is applied. For example, some embodiments use a therapy period of approximately one day, and use a therapy duration of approximately 8 hours each day. These parameter(s) can represent limits (e.g. maximum, minimum, range) for the parameter values. Some embodiments, for example, use the therapy duration parameter as a minimum value, such that at least that duration of the therapy will be applied per therapy period (e.g. at least 8 hours of therapy per day). The delivered therapy can be intermittent or continuous. Some scheduler embodiments use parameter(s) to control intermittent stimulation during the therapy period, such as duty cycle 1528 or stimulation period 1529. The duty cycle represents the percentage of time during which stimulation is delivered for a stimulation period. A therapy period (e.g. on the order of a day) can include many stimulation periods (e.g. less than five minutes or on the order of one minute). Some embodiments limit the duty cycle to less than approximately 50%, some embodiments limit the duty cycle to less than approximately 25%, and some embodiments limit the duty cycle to a range between and including 10% and 20%. However, other duty cycles can be used. A scheduler embodiment implements a protocol where neural stimulation is delivered for approximately ten seconds every minute (e.g. duty cycle of approximately 17% and a stimulation period of approximately one minute). The scheduler parameters can include start and stop parameters, start and duration parameters, or other parameters that can be used to control the schedule of neural stimulation. Some of the parameter examples can be derived from others (e.g. start and stop times can be derived from start and duration). Some embodiments of the scheduler program or limit the stimulation period, where a train of neural stimulation pulses occurs with each stimulation period. For example, some embodiments limit or program the stimulation period to a value less than five minutes, and some embodiments limit or program the stimulation period to a value on the order of one minute (e.g. 50 seconds).

The illustrated controller also includes a module to control neural stimulation intensity 1530. Therapy inputs and/or therapy feedback can be used to appropriately adjust one or more stimulation parameter(s) to increase, decrease or maintain a desired neural stimulation intensity. For example, the amplitude, frequency, and/or pulse width of a neural stimulation pulse train can be adjusted to titrate the neural stimulation intensity. Some embodiments adjust the neural stimulation schedule to adjust the neural stimulation intensity. Examples of schedule parameters include therapy duration, start/stop times, stimulation period, stimulation train duration per stimulation period, and duty cycle. For embodiments that allow some schedule parameters to be modified, the scheduler limits the extent of any allowed modifications to the schedule parameters. For example, the duty cycle of the stimulation can be adjusted to a value less than or equal to the maximum duty cycle (e.g. 50%) permitted by the scheduler or within a range of duty cycles permitted by the scheduler. In another example, the therapy duration can be adjusted to a value greater than or equal to the minimum value (e.g. 8 hours per day) for the duration of the therapy permitted by the controller.

Advanced patient management systems can be used to enable the patient and/or doctor to adjust parameter(s) to avoid observed or sensed habituation, or to adjust therapy intensity. The inputs can be provided by computers, programmers, cell phones, personal digital assistants, and the like. The patient can call a call center using a regular telephone, a mobile phone, or the internet. The communication can be through a repeater, similar to that used in Boston Scientific's Latitude patient management system. In response, the call center (e.g. server in call center) can automatically send information to the device to adjust or titrate the therapy. The call center can inform the patient's physician of the event. A device interrogation can be automatically triggered. The results of the device interrogation can be used to determine if and how the therapy should be adjusted and/or titrated to improve the transient response. A server can automatically adjust and/or titrate the therapy using the results of the device interrogation. Medical staff can review the results of the device interrogation, and program the device through the remote server to provide the desired therapy adjustments and/or titrations. The server can communicate results of the device interrogation to the patient's physician, who can provide input or direction for adjusting and/or titrating the therapy.

Figure 16:
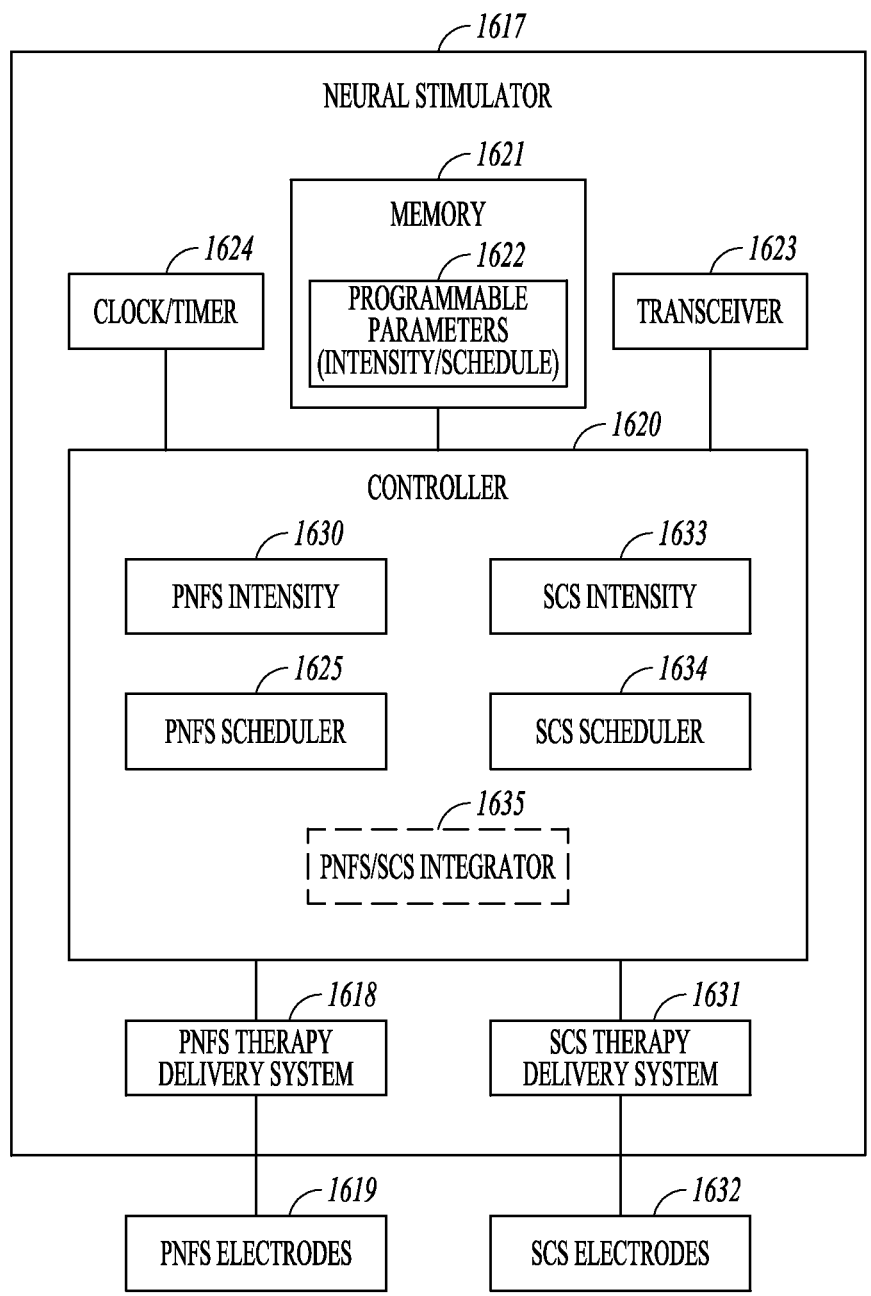
FIG. 16 illustrates an embodiment of a device configured to deliver PNFS and SCS.

In some embodiments, the PNFS is combined with SCS to provide a desired therapy. FIG. 16 illustrates a device configured to deliver PNFS and SCS. The illustrated device 1617 includes a PNFS therapy delivery system 1618 adapted to deliver a neural stimulation signal to the PNFS electrode(s) 1619 to deliver the PNFS therapy to the desired intercostal nerves, and further includes and an SCS therapy deliver system 1631 adapted to deliver a neural stimulation signal to the SCS electrode(s) 1632 to deliver the SCS therapy to the desired region of the spinal cord. A controller 1620 appropriately controls the delivery systems to provide the appropriate neural stimulation signals to the PNFS and SCS electrode(s). The illustrated device includes a memory 1621 to store programmable parameters 1622. The controller implements a PNFS therapy and a SCS therapy using the programmable parameters. Examples of programmable parameters, any one or more of which can be stored in the memory, include a therapy duration parameter, a therapy period, as well as a duty cycle, and a stimulation therapy for intermittent stimulation. The programmable parameters can also include parameters used to adjust the intensity of the neural stimulation therapy, such as amplitude, frequency, pulse width, and stimulation schedule parameters. The illustrated device includes a transceiver 1623 adapted to communicate with an external device (e.g. programmer) for use in receiving programming instructions. In some embodiments, the device may include at least one port for receiving neural stimulation therapy inputs or neural stimulation feedback inputs (including both therapy and feedback inputs according to some embodiments). The input can receive a communication from a device programmer, for use by a physician or patient in changing the programmable parameters based on observed conditions. The input can receive feedback from physiologic sensors used to monitor physiologic responses to the neural stimulation. Examples of such sensors used to provide feedback for the transition protocol include heart rate and blood pressure sensors.

The illustrated device includes a clock/timer 1624, used by the controller to control timing of the neural stimulation signals for the neural stimulation therapy. The illustrated controller includes a neural stimulation scheduler, which uses the clock/timer and schedule parameter(s) to control the stimulation delivered by the delivery system.

The controller 1620 may include a controller to control the PNFS intensity 1630 and a PNFS scheduler 1625 to control the timing of the PNFS therapy, which may function similarly to 1530 and 1525 in FIG. 15. The controller 1620 may include a controller to control the intensity of the SCS therapy 1633 and an SCS scheduler 1634 to control the timing of the SCS therapy. Some embodiments of the device 1617 include a PNFS/SCS integrator 1635 that functions to integrate or coordinate the PNFS and SCS therapies delivered by the device. In some embodiments PNFS and SCS electrodes may be activated simultaneously to achieve broad regions of paresthesia across the left chest in the distribution of typical anginal pain. In some embodiments, the PNFS electrodes may be programmed alone, with anodes and cathodes all placed on a single lead, or with one lead carrying all anodes and the other lead carrying all cathodes. Paresthesia may or may not be generated, as the stimulation may be generated with a non-zero, sub perceptible intensity. Rather than incorporating the PNFS therapy deliver system and SCS therapy delivery system within the same implantable device, some embodiments provide a system with separate implantable devices, where one device provides the PNFS therapy and another device provides the SCS therapy. The system may be configured to independently provide the PNFS therapy and the SCS therapy, or may be designed to coordinate the PNFS and SCS therapies.

Figure 17:
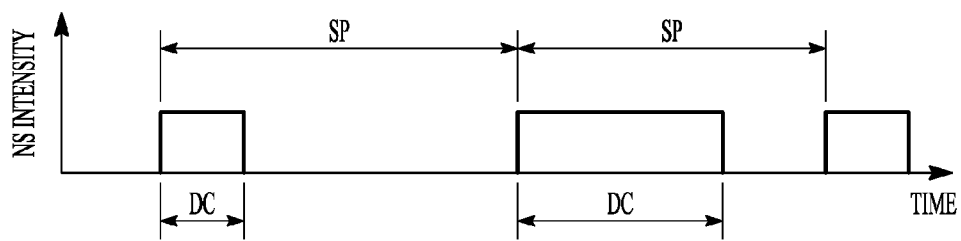
FIGS. 17-18 illustrate examples of intermittent neural stimulation.
Figure 18:
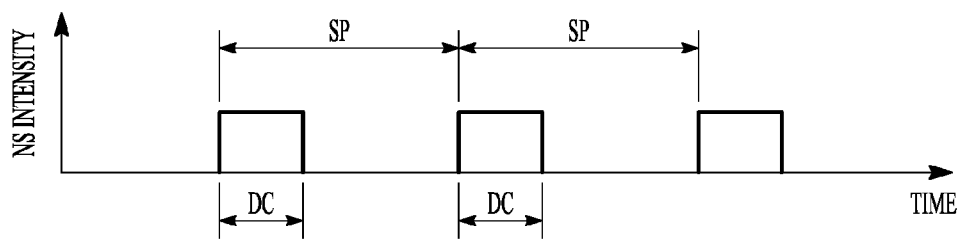

Various embodiments of the present subject matter deliver intermittent neural stimulation. For example, intermittent neural stimulation may be delivered to treat chronic diseases such as heart failure and hypertension. Some of the terms used to discuss intermittent stimulation are illustrated in FIGS. 17 and 18. Intermittent neural stimulation can be delivered using a duty cycle of a stimulation period. FIGS. 17 and 18 plot neural stimulation intensity against time. FIG. 17 illustrates variable stimulation periods (SP) and duty cycles (DC), and FIG. 18 illustrates constant stimulation periods (SP) and duty cycles (DC). Each duty cycle can include a train of neural stimulation pulses. The duty cycle and stimulation period need not be constant throughout the Neuro Stimulation Therapy (NST). For example, the duration or frequency of the duty cycle can be adjusted to adjust an intensity of the NST. Also, the start and/or stop of the duty cycle can be dependent on enabling conditions. The duty cycle and/or stimulation period can be adjusted in every subsequent stimulation period. Unless expressly disclosed otherwise herein, "stimulation period" and "duty cycle" are not intended to only encompass constant values that result in neural stimulation in a precise periodic manner (e.g. FIG. 18), but rather is intended to include intermittent neural stimulation where therapeutically-effective or prophylactically-effective neural stimulation is delivered for a time and then not delivered for a time, and then delivered for a time (e.g. FIG. 17). In electrical stimulation, for example, a train of neural stimulation pulses (current or voltage) can be delivered during a duty cycle of stimulation. Stimulation waveforms can be square pulses or other shapes. The stimulation pulses can be monophasic or biphasic pulses.

Figure 19:
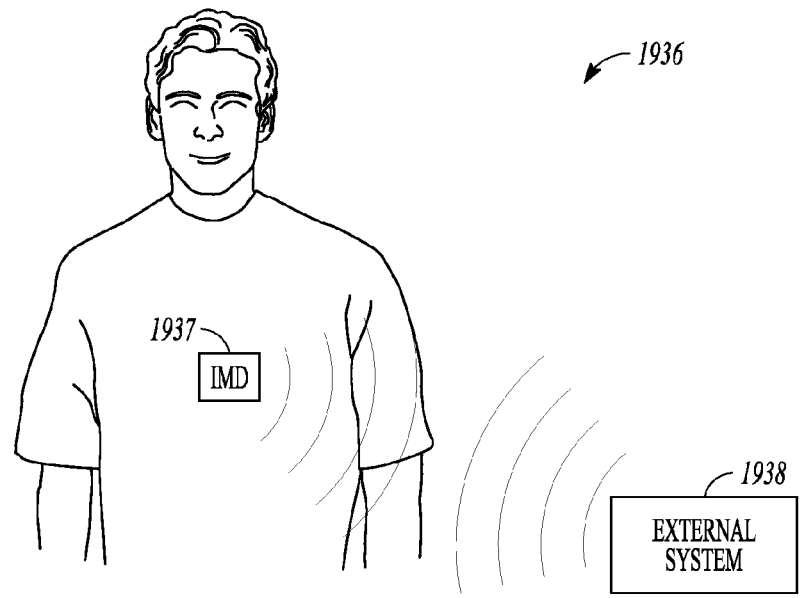
FIG. 19 illustrates an embodiment of a system including an implantable medical device (IMD) and an external system or device.

FIG. 19 illustrates a system 1936 including an implantable medical device (IMD) 1937 and an external system or device 1938, according to various embodiments of the present subject matter. According to various embodiments, the IMD delivers PNFS to intercostal nerves to inhibit a sympathetic response. In some embodiments, the IMD delivers PNFS to intercostal nerves and SCS to a spinal cord to inhibit sympathetic effects. Various embodiments of the IMD include NS functions such as PNFS or include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example.

Physiological sensor(s) can be used to sense physiological response(s) to the therapy(ies) delivered by the IMD. In some embodiments, a physiological sensor or sensors are used to sense a physiological response to the PNFS or to the PNFS and SCS. The sensed physiological response can be used to provide feedback control of the PNFS or the PNFS and SCS. Examples of physiological responses include cardiac activity such as heart rate, HRV, PR interval, T-wave velocity, and action potential duration. Other examples of physiological responses include hemodynamic responses such as blood pressure, and respiratory responses such as tidal volume and minute ventilation. The controller circuitry can control the therapy provided by a system using a therapy schedule and a therapy titration routine in memory, or can compare a target range (or ranges) of the sensed physiological response(s)

stored in the memory to the sensed physiological response(s) to appropriately adjust the intensity of the neural stimulation/inhibition.

The external system allows a user such as a physician or other caregiver or a patient to control the operation of the IMD and obtain information acquired by the IMD. In one embodiment, the external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from the implantable medical device to the external system. This includes, for example, transmitting real-time physiological data acquired by the IMD, extracting physiological data acquired by and stored in the IMD, extracting therapy history data stored in the implantable medical device, and extracting data indicating an operational status of the IMD (e.g., battery status and lead impedance). The telemetry link also provides for data transmission from the external system to the IMD. This includes, for example, programming the IMD to acquire physiological data, programming the IMD to perform at least one self-diagnostic test (such as for a device operational status), and programming the IMD to deliver at least one therapy.

Figure 20:
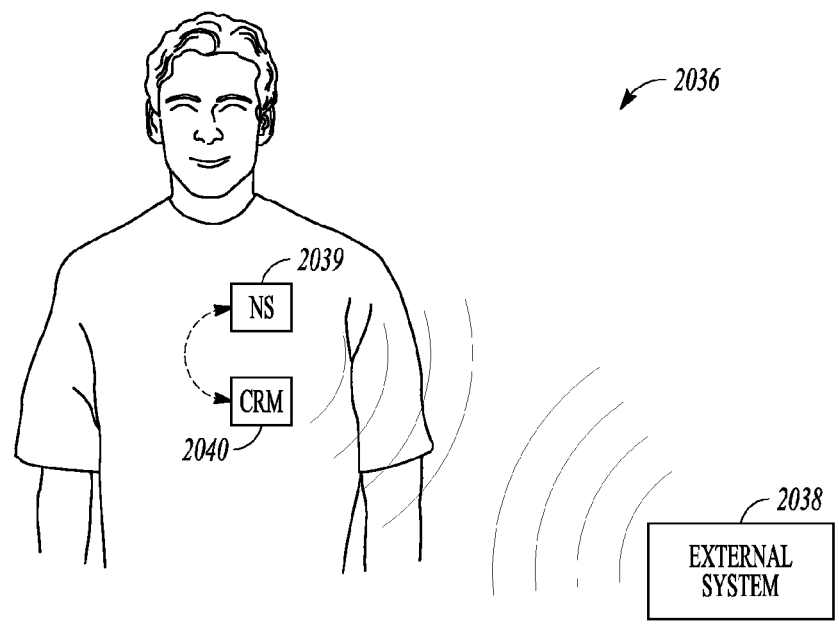
FIG. 20 illustrates an embodiment of a system including an external device, an implantable neural stimulator (NS) device and an implantable cardiac rhythm management (CRM) device.

FIG. 20 illustrates a system 2036 including an external device 2038, an implantable neural stimulator (NS) device 2039 and an implantable cardiac rhythm management (CRM) device 2040, according to various embodiments of the present subject matter. In some embodiments, the NS device is configured to only deliver PNFS. In some embodiments, the NS device is configured to deliver PNFS along with SCS, or vagal nerve stimulation (VNS), or both SCS and VNS. In some embodiments, the different neural stimulation therapies are implemented using separate devices rather than a single NS device. Various embodiments are configured to enable communication between an NS device and a CRM device or other cardiac stimulator. In various embodiments, this communication allows one of the devices to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices. According to various embodiments, the NS device is a PNFS device or a combination PNFS and SCS device. According to various embodiments, the illustrated NS device includes two or more implantable devices configured to communicate with each other.

Examples of NS and CRM devices cooperating to deliver heart failure therapy include: U.S. Pat. No. 7,657,312, filed Nov. 3, 2003 and entitled "Multi-Site Ventricular Pacing Therapy With Parasympathetic Stimulation;" U.S. Pat. No. 7,260,431, filed May 20, 2004 and entitled "Combined Remodeling Control Therapy and Anti-Remodeling Therapy By Implantable Cardiac Device;" and U.S. Pat. No. 7,587,238, filed Mar. 11, 2005, and entitled "Combined Neural Stimulation and Cardiac Resynchronization Therapy." Examples of NS and CRM devices cooperating to respond to myocardial infarction and arrhythmias include U.S. Pat. No. 7,509,166, filed Dec. 24, 2003 and entitled "Automatic Baroreflex Modulation Responsive To Adverse Event;" and U.S. Pat. No. 7,689,286, filed May 2, 2006 and entitled "Myocardium Conditioning Using Myocardial and Parasympathetic Stimulation."

Other examples of cooperating between NS and CRM devices include: U.S. Pat. No. 7,493,161, filed May 10, 2005 and entitled "System and Method to Deliver Therapy in Presence of Another Therapy;" U.S. Pat. No. 7,551,958, filed May 24, 2005 and entitled "Safety Control System for Implantable Neural Stimulator;" U.S. Pat. No. 7,542,800, filed Apr. 5, 2005 and entitled "Method and Apparatus for Synchronizing Neural Stimulation to Cardiac Cycles;" and U.S. Pat. No. 7,672,728, filed Dec. 28, 2005 and entitled "Neural Stimulator to Treat Sleep Disordered Breathing." U.S. Pat. Nos. 7,657,312, 7,260,431, 7,587,238, 7,509,166, 7,689,286, 7,493,161, 7,542,800 and 7,672,728 are incorporated by reference in their entirety.

NS and CRM devices can cooperate to provide anti-arrhythmia treatment (prevent, suppress, or terminate atrial and/or ventricular arrhythmias). For example, U.S. Pub. App. No. 2008/0086174, filed Oct. 4, 2006 and entitled "System For Neurally-Mediated Anti-Arrhythmic Therapy" describe, among other things, a method where a predetermined cardiac activity indicated for an antitachycardia shock is detected. Neural stimulation is applied to lower a defibrillation threshold in preparation for the shock, and the shock is subcutaneously delivered using subcutaneous, non-intrathoracic electrodes. According to one embodiment, neural stimulation is applied as part of a prophylactic therapy. A predetermined cardiac activity indicated for an antitachycardia shock is detected, and the shock is subcutaneously delivered. Additionally or alternatively, neural stimulation may be used to control pain associated with the shock. U.S. Pub. App. No. 2008/0086174 is incorporated herein by reference in its entirety. Neural stimulation may be used to modify an arrhythmia into a modified arrhythmia that is more likely to be successfully treated. For example, U.S. Pub. App. No. 2007/0260283, field May 8, 2006 and entitled "Method and Device for Providing Anti-Tachyarrhythmia Therapy" uses neural stimulation to modify ventricular tachycardia into a modified arrhythmia that may be treated using anti-tachycardia pacing. Neural stimulation may be used to provide diagnostic stimulation for arrhythmia recognition, such as is disclosed in U.S. Pub. App. No. 2010/0036447, filed Aug. 4, 2009 and entitled "Neural Stimulation For Arrhythmia Recognition and Therapy" and U.S. Pub. App. No. 2011/0218586, filed Feb. 2, 2011 and entitled "Methods and Systems for Recognizing Arrhythmias Using Neural Stimulation." U.S. Pub. App. No. 2010/0036447 and U.S. Pub. App. No. 2011/0218586 are incorporated by reference in their entirety.

Figure 21:
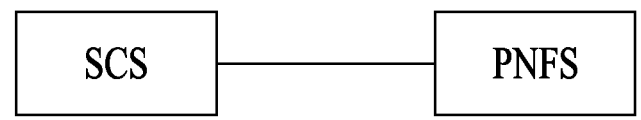
FIG. 21 illustrates an embodiment of a system comprising a SCS device and a PNFS device.

FIG. 21 illustrates a system comprising a SCS device and a PNFS device. Both the SCS device and the PNFS device are implantable devices. Further, in some embodiments the SCS device and the PNFS device are configured to communicate with each other. For example, such communication may be used to coordinate the delivery of the SCS and PNFS. The communication may be over a wired connection between the SCS device or the PNFS device, or may be over a wireless connection between the devices. Examples of wireless connections include ultrasound, radiofrequency and inductive communications.

Figure 22:
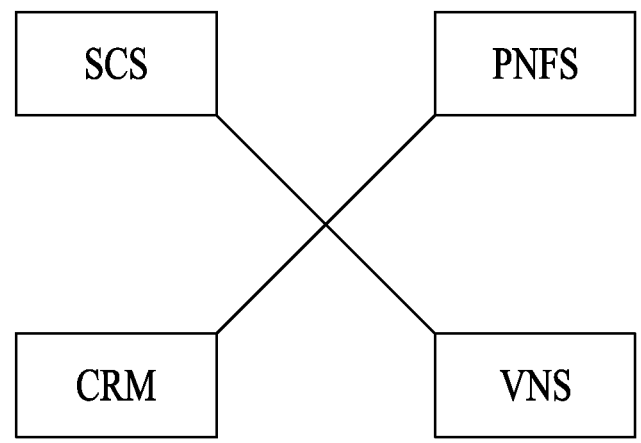
FIG. 22 illustrates an embodiment of a system comprising a SCS device and a PNFS device.

FIG. 22 illustrates a system comprising a SCS device and a PNFS device. The illustrated system further includes a CRM device, a vagal nerve stimulator (VNS), or both a CRM device and VNS. All of the devices may be implantable. Further, in some embodiments at least some of the devices are configured to communicate with each other. For example, such communication may be used to coordinate the delivery of the SCS and PNFS and the VNS and the CRM therapies. The communication may be over wired connections or wireless connections. The communication may involve a network communication protocol to enable one device to address communication to any other device. Other communication protocols may be used. By way of example and not limitation, a time division multiplexing scheme may be used to provide each device a time slot in which they can broadcast messages.

Figure 23:
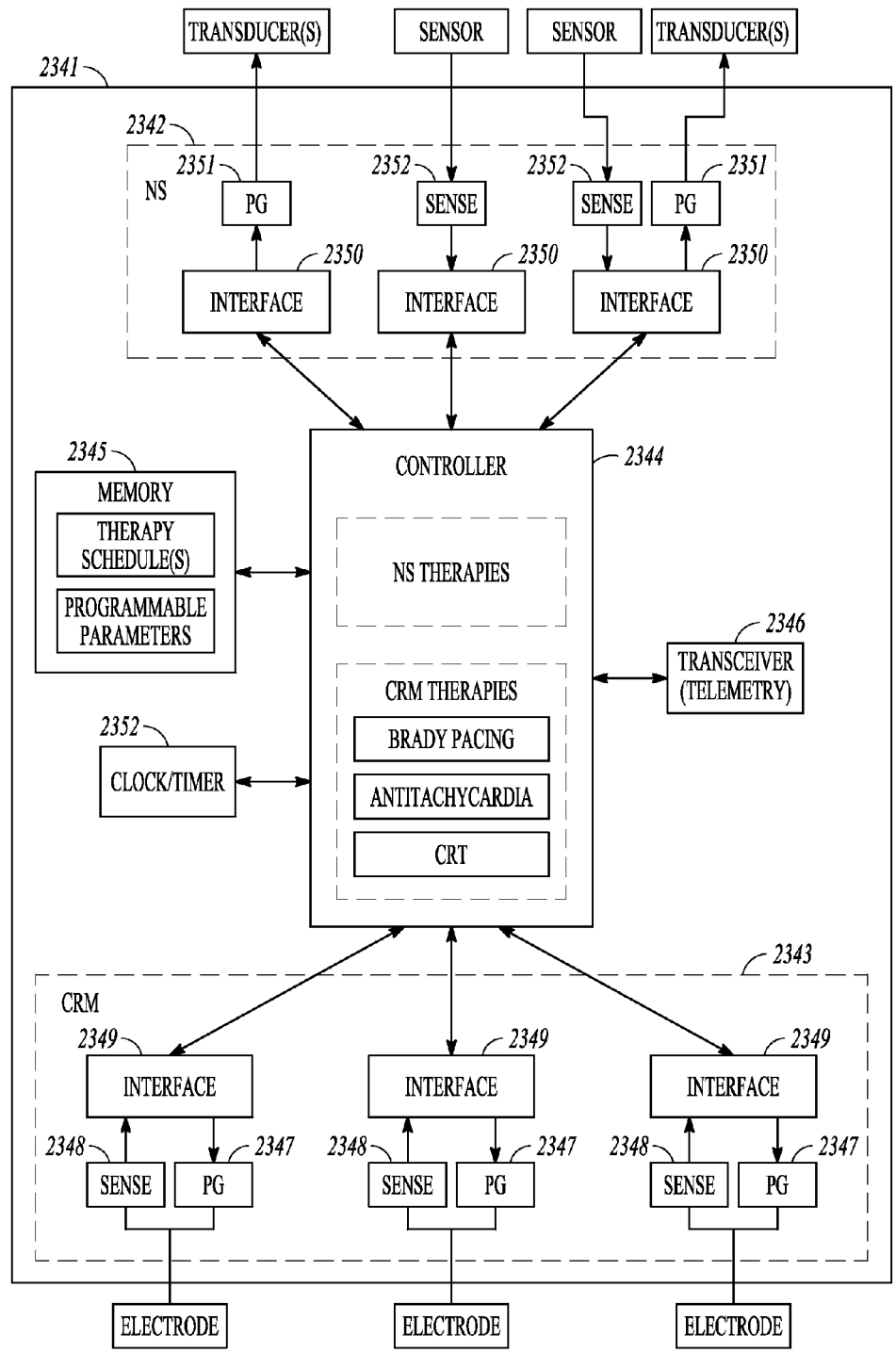
FIG. 23 illustrates an embodiment of an implantable medical device (IMD) having a neural stimulation (NS) component and a cardiac rhythm management (CRM) component.

FIG. 23 illustrates an implantable medical device (IMD) 2341 having a neural stimulation (NS) component 2342 and a cardiac rhythm management (CRM) component 2343 according to various embodiments of the present subject matter. The illustrated device includes a controller 2344 and memory 2345. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by one or more processors. For example, therapy schedule(s) and programmable parameters can be stored in memory. According to various embodiments, the controller includes a processor to execute instructions embedded in memory to perform the neural stimulation and CRM functions. The illustrated neural stimulation therapy can include a PNFS therapy, and may also include other neural stimulation therapy such as SCS or VNS therapies. Various embodiments include CRM therapies, such as bradycardia pacing, anti-tachycardia therapies such as anti-tachycardia pacing (ATP), defibrillation and cardioversion, and cardiac resynchronization therapy (CRT). The illustrated device further includes a transceiver 2346 and associated circuitry for use to communicate with a programmer or another external or internal device. Various embodiments include a telemetry coil.

The CRM therapy section includes components, under the control of the controller, to stimulate a heart and/or sense cardiac signals using one or more electrodes. The illustrated CRM therapy section 2343 includes a pulse generator 2347 for use to provide an electrical signal through an electrode to stimulate a heart, and further includes sense circuitry 2348 to detect and process sensed cardiac signals. An interface 2349 is generally illustrated for use to communicate between the controller and the pulse generator and sense circuitry. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 2342 includes components, under the control of the controller, to stimulate a neural stimulation target and/or sense parameters associated with nerve activity or surrogates of nerve activity such as blood pressure and respiration. Three interfaces 2350 are illustrated for use to provide neural stimulation. However, the present subject matter is not limited to a particular number interfaces, or to any particular stimulating or sensing functions. Pulse generators 2351 are used to provide electrical pulses to transducer or transducers for use to stimulate a neural stimulation target. According to various embodiments, the pulse generator includes circuitry to set, and in some embodiments change, the amplitude of the stimulation pulse, the pulse width of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. The system is configured to use the pulse generator to provide therapeutically effective PNFS. Sense circuits 2352 are used to detect and process signals from a sensor, such as a sensor of nerve activity, blood pressure, respiration, and the like. The interfaces are generally illustrated for use to communicate between the controller and the pulse generator and sense circuitry. Each interface, for example, may be used to control a separate lead. Various embodiments of the NS therapy section only include a pulse generator to stimulate a neural target. The illustrated device further includes a clock/timer 2352, which can be used to deliver the programmed therapy according to a programmed stimulation protocol and/or schedule.

Figure 24:
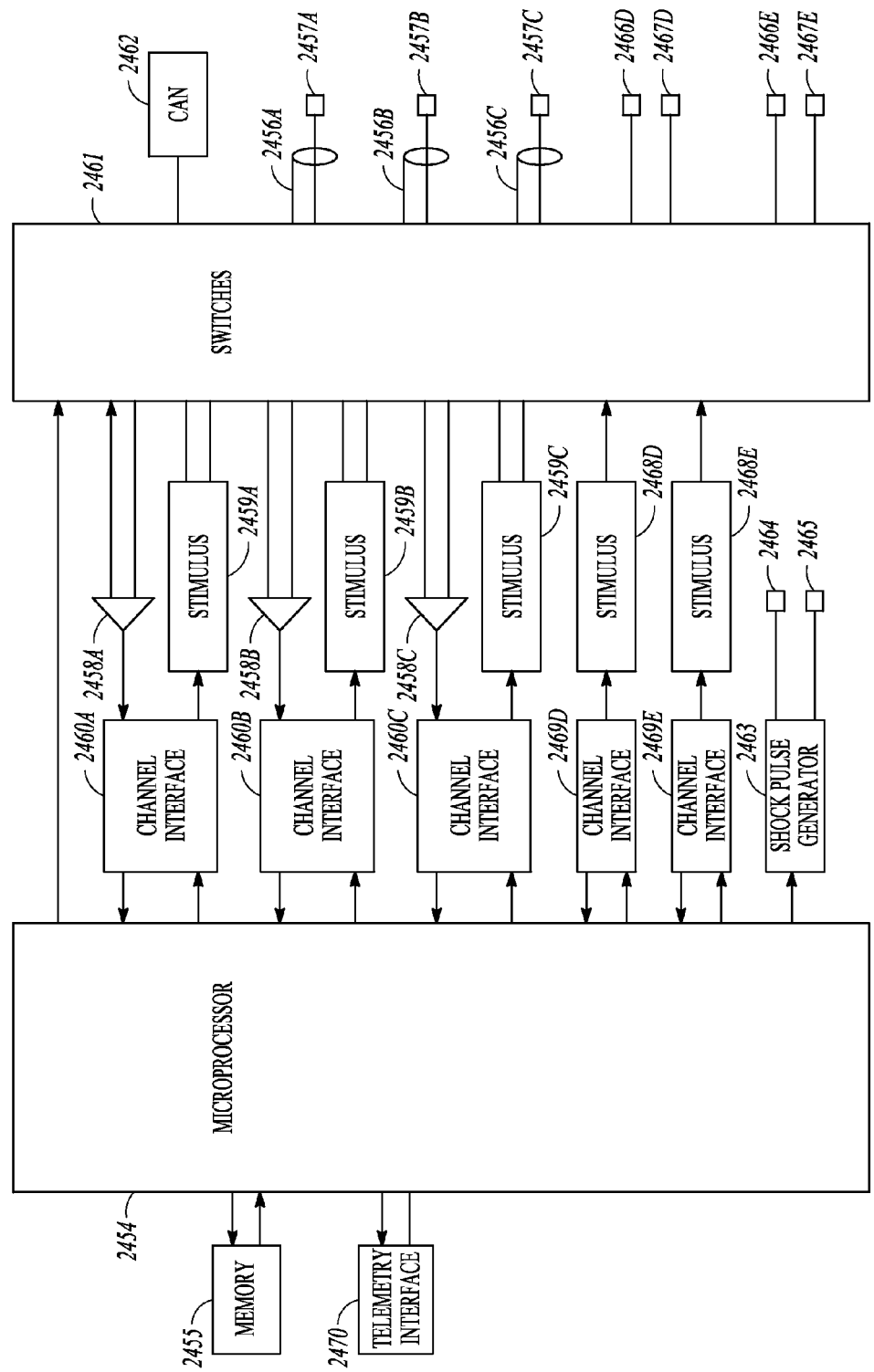
FIG. 24 illustrates an embodiment of a microprocessor-based implantable device.

FIG. 24 shows a system diagram of an embodiment of a microprocessor-based implantable device, according to various embodiments. The controller of the device is a microprocessor 2454 which communicates with a memory 2455 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 2456A-C and tip electrodes 2457A-C, sensing amplifiers 2458A-C, pulse generators 2459A-C, and channel interfaces 2460A-C. Each channel thus includes a pacing channel made up of the pulse generator connected to the electrode and a sensing channel made up of the sense amplifier connected to the electrode. The channel interfaces 2460A-C communicate bidirectionally with the microprocessor 2454, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 2461 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 2462 or an electrode on another lead serving as a ground electrode. A shock pulse generator 2463 is also interfaced to the controller for delivering a defibrillation shock via shock electrodes 2464 and 2465 to the atria or ventricles upon detection of a shockable tachyarrhythmia.

Neural stimulation channels, identified as channels D and E, are incorporated into the device for delivering autonomic modulation, where one channel includes a bipolar lead with a first electrode 2466D and a second electrode 2467D, a pulse generator 2468D, and a channel interface 2469D, and the other channel includes a bipolar lead with a first electrode 2466E and a second electrode 2467E, a pulse generator 2468E, and a channel interface 2469E. The neural stimulation is not limited to the use of two electrodes on a lead, as multiple electrodes may be used to deliver the PNFS or other neural stimulation. Some embodiments may use unipolar leads in which case the neural stimulation pulses are referenced to the can or another electrode. Some embodiments may use tripolar or multipolar leads. In various embodiments, the pulse generator for each channel outputs a train of neural stimulation pulses which may be varied by the controller as to amplitude, frequency, duty-cycle, and the like. In this embodiment, each of the neural stimulation channels uses a lead which can be subcutaneously, intramuscularly, epineurally, endoneurally, epidurally, subdurally, intraneurally, periosteally, or intravascularly disposed near an appropriate neural target. Other types of leads and/or electrodes may also be employed. In some embodiments, the leads of the neural stimulation electrodes are replaced by wireless links.

The figure illustrates a telemetry interface 2470 connected to the microprocessor, which can be used to communicate with an external device. The illustrated microprocessor is capable of performing neural stimulation therapy routines and myocardial (CRM) stimulation routines. Examples of NS therapy routines include PNFS therapies to treat ventricular remodeling, hypertension, and heart failure. The present subject matter is not limited to a particular neural stimulation therapy. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

Figure 25:
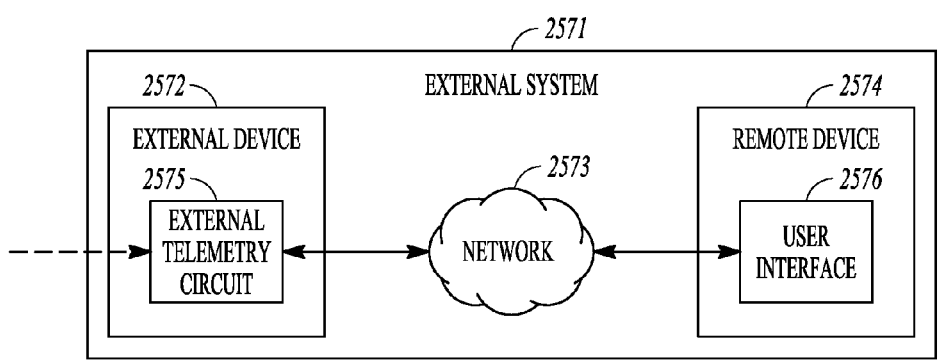
FIG. 25 is a block diagram illustrating an embodiment of an external system.

FIG. 25 is a block diagram illustrating an embodiment of an external system. The external system includes a programmer, in some embodiments. In the illustrated embodiment, the external system includes a patient management system. As illustrated, the external system is a patient management system 2571 including an external device 2572, a telecommunication network 2573, and a remote device 2574. The external device is placed within the vicinity of an implantable medical device (IMD) and includes an external telemetry system 2575 to communicate with the IMD. The remote device(s) is in one or more remote locations and communicates with the external device through the network, thus allowing a physician or other caregiver to monitor and treat a patient from a distant location and/or allowing access to various treatment resources from the one or more remote locations. The illustrated remote device includes a user interface 2576. According to various embodiments, the external device includes a neural stimulator, a programmer or other device such as a computer, a personal data assistant or phone. The external device, in various embodiments, includes two devices adapted to communicate with each other over an appropriate communication channel, such as a computer by way of example and not limitation. The external device can be used by the patient or physician to provide side effect feedback indicative of patient discomfort, for example.

One of ordinary skill in the art will understand that, the modules and other circuitry shown and described herein can be implemented using software, hardware, firmware and combinations thereof. As such, the terms module and circuitry, for example, are intended to encompass software implementations, hardware implementations, firmware implementations, and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
delivering a cardiovascular therapy, wherein delivering the cardiovascular therapy includes delivering neural modulation to treat a cardiovascular condition, wherein delivering neural modulation to treat the cardiovascular condition includes delivering a neural modulation therapy selected from the group of neuromodulation therapies consisting of: a heart failure therapy a myocardial infarction (MI) therapy, a post-MI remodeling therapy, a hypertension therapy, and an anti-arrhythmia therapy,
wherein delivering neural modulation to treat the cardiovascular condition includes delivering a peripheral nerve field modulation (PNFM) to peripheral nerve fields of one or more of the intercostal nerves extending to and from a T1-T5 region of a spinal cord.

2. The method of claim 1, wherein delivering neural modulation to treat the cardiovascular condition further includes delivering spinal cord modulation (SCM) therapy to one or more neural targets in the T1-T5 region of the spinal cord.

3. The method of claim 1, further comprising implanting the PNFM electrodes in a subcutaneous space parasternally to modulate peripheral nerve fields extending to and from the intercostal nerves projecting from the T1-T5 region of the spinal cord.

4. The method of claim 3, wherein delivering the PNFM includes delivering monopolar modulation using the PNFM electrodes as cathode electrodes.

5. The method of claim 3, wherein delivering the PNFM includes delivering bipolar modulation using at least one of the PNFM electrodes as a cathode electrode and using at least another one of the PNFM electrodes as an anode electrode.

6. The method of claim 1, further comprising implanting the PNFM electrodes in a subcutaneous space paraspinally to modulate peripheral nerve fields of one or more of the intercostal nerves extending to and from the T1-T5 region of the spinal cord.

7. The method of claim 6, wherein delivering the PNFM includes delivering monopolar modulation using the PNFM electrodes as cathode electrodes.

8. The method of claim 6, wherein delivering the PNFM includes delivering bipolar modulation using at least one of the PNFM electrodes as a cathode electrode and using at least another one of the PNFM electrodes as an anode electrode.

9. The method of claim 1, further comprising implanting a lead with some of the PNFM electrodes in a subcutaneous non-intrathoracic space parasternally and implanting another lead with other of the PNFM electrodes in a subcutaneous non-intrathoracic space paraspinally to modulate peripheral nerve fields of one or more of the intercostal nerves extending to and from the T1-T5 region of the spinal cord.

10. The method of claim 9, wherein delivering the PNFM includes using the PNFM electrodes from one of the leads as anode electrodes and using the PNFM electrodes from the other one of the leads as cathode electrodes.

11. The method of claim 1, wherein the cardiac condition includes heart failure and the cardiovascular therapy includes heart failure therapy, and delivering neural modulation to treat the cardiovascular condition further includes delivering PNFM to treat the heart failure.

12. The method of claim 11, wherein delivering the cardiovascular therapy includes delivering myocardial stimulation to treat the heart failure.

13. The method of claim 11, wherein delivering the cardiovascular therapy includes delivering spinal cord modulation (SCM) to treat the heart failure.

14. The method of claim 11, wherein delivering the cardiovascular therapy includes delivering vagal nerve stimulation (VNS) to treat the heart failure.

15. The method of claim 1, wherein delivering neural modulation for the cardiovascular therapy includes delivering PNFM in response to a myocardial infarction.

16. The method of claim 1, wherein:
delivering neural modulation to treat the cardiovascular condition includes delivering an anti-arrhythmia stimulation selected from the group of:
suppressing atrial arrhythmias;
suppressing ventricular arrhythmias;
preventing atrial arrhythmias;
preventing ventricular arrhythmias;
terminating atrial arrhythmias; and
terminating ventricular arrhythmias; and
delivering the anti-arrhythmia stimulation includes delivering PNFM.

17. The method of claim 1, further comprising sensing a condition indicated for shocking the heart, wherein delivering neural modulation to treat the cardiovascular therapy includes delivering PNFM in response to sensing the condition and in anticipation of shocking the heart, the method further comprising using subcutaneous electrodes to shock the heart.

18. A method, comprising:
delivering a heart failure therapy, wherein delivering the heart failure therapy includes modulating peripheral nerve fields of intercostal nerves extending to and from a T1-T5 region of a spinal cord to treat heart failure.

19. The method of claim 18, wherein delivering the heart failure therapy further includes using a spinal cord modulator to modulate neural targets in the T1-T5 region of the spinal cord.

20. The method of claim 18, wherein delivering the heart failure therapy further includes stimulating myocardial tissue, wherein stimulating myocardial tissue includes delivering a cardiac resynchronization therapy (CRT).

21. The method of claim 18, wherein delivering the heart failure therapy further includes stimulating a vagus nerve.

22. A method, comprising:
delivering a heart failure therapy, wherein delivering the heart failure therapy includes modulating peripheral nerve fields of intercostal nerves extending to and from a T1-T5 region of a spinal cord to treat heart failure, wherein modulating peripheral nerve fields of intercostal nerves extending to and from the T1-T5 region includes using peripheral nerve field modulation (PNFM) electrodes implanted within a subcutaneous space parasternally or using PNFM electrodes implanted within a subcutaneous space paraspinally.

23. The method of claim 22, wherein modulating peripheral nerve fields of intercostal nerves includes delivering monopolar modulation using the PNFM electrodes as cathode electrodes.

24. The method of claim 22, wherein modulating peripheral nerve fields of intercostal nerves includes delivering bipolar modulation using at least one of the PNFM electrodes as a cathode electrode and using at least another one of the PNFM electrodes as an anode electrode.

25. The method of claim 22, wherein using PNFM electrodes includes both using PNFM electrodes implanted within the subcutaneous space parasternally and using PNFM electrodes implanted within the subcutaneous space paraspinally.

* * * * *